(12) United States Patent
Hommeltoft et al.

(10) Patent No.: US 8,288,601 B2
(45) Date of Patent: Oct. 16, 2012

(54) PROCESS FOR REACTING AN ISO-ALKANE TO PRODUCE A HIGH BOILING PRODUCT AND AN ALKYLATE GASOLINE BLENDING COMPONENT

(75) Inventors: Sven Ivar Hommeltoft, Pleasant Hill, CA (US); Hye Kyung Cho Timken, Albany, CA (US); Steve Sarup Mathur, Danville, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 13/471,176

(22) Filed: May 14, 2012

(65) Prior Publication Data
US 2012/0226083 A1 Sep. 6, 2012

Related U.S. Application Data

(62) Division of application No. 12/628,020, filed on Nov. 30, 2009, now Pat. No. 8,247,628.

(51) Int. Cl.
*C07C 2/56* (2006.01)
*C07C 2/06* (2006.01)
(52) U.S. Cl. ......... 585/331; 585/332; 585/521; 585/709
(58) Field of Classification Search .................. 585/331, 585/332, 521, 709
See application file for complete search history.

(56) References Cited

U.S. PATENT DOCUMENTS

| | | | |
|---|---|---|---|
| 6,849,773 B2 | 2/2005 | Podrebarac et al. |
| 6,919,016 B2 | 7/2005 | Podrebarac et al. |
| 7,432,409 B2 | 10/2008 | Elomari et al. |
| 7,449,612 B2 | 11/2008 | Smith et al. |
| 7,531,707 B2 | 5/2009 | Harris et al. |
| 7,566,799 B2 | 7/2009 | Steinbrenner et al. |
| 7,569,740 B2 | 8/2009 | Elomari |
| 7,601,861 B2 | 10/2009 | Bottke et al. |
| 7,919,664 B2 | 4/2011 | Hommeltoft et al. |
| 7,923,593 B2 | 4/2011 | Hommeltoft et al. |
| 7,955,495 B2 | 6/2011 | Hommeltoft et al. |
| 2008/0045763 A1 | 2/2008 | Cross et al. |
| 2008/0146858 A1 | 6/2008 | Elomari et al. |
| 2009/0192339 A1 | 7/2009 | Timken et al. |

FOREIGN PATENT DOCUMENTS
EP 1868968 12/2009

OTHER PUBLICATIONS
CDTECH, 2006 Q&A and Technology Forum slide, NPRA, Q#30.

*Primary Examiner* — Thuan D Dang
(74) *Attorney, Agent, or Firm* — Susan M. Abernathy

(57) ABSTRACT

A process for reacting an iso-alkane, comprising:
a) partially converting one or more olefins in an olefinic feedstock to make a converted olefinic feedstock, wherein the converting is different from isomerization;
b) isolating from the converted olefinic feedstock:
 i. an enriched feed that has linear internal olefins, and
 ii. products having a boiling point of 150° C. or higher; and
c) alkylating the iso-alkane with the enriched feed to make an alkylate gasoline blending component.

14 Claims, 1 Drawing Sheet

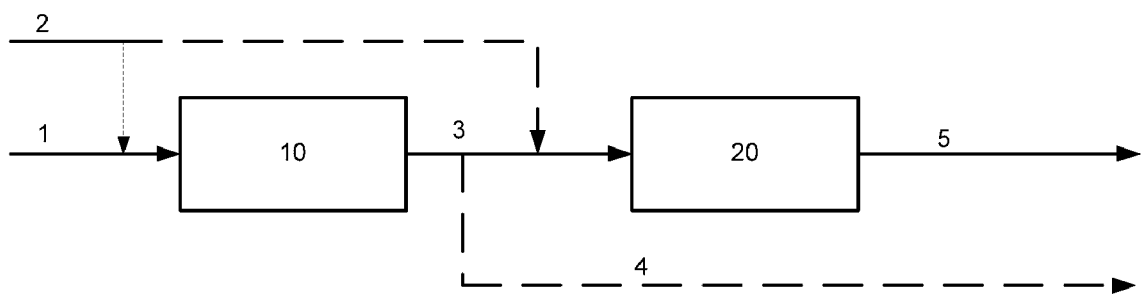

PROCESS FOR REACTING AN ISO-ALKANE TO PRODUCE A HIGH BOILING PRODUCT AND AN ALKYLATE GASOLINE BLENDING COMPONENT

This application is a divisional of U.S. patent application Ser. No. 12/628,020, filed Nov. 30, 2009, now U.S. Pat. No. 8,247,628; and herein incorporated in its entirety. This application also claims priority to U.S. patent application Ser. No. 12/628,009, filed Nov. 30, 2009; also herein incorporated in its entirety.

TECHNICAL FIELD

This application is directed to process for reacting an iso-alkane to produce one or more products having a boiling point of at least 150° C. and an alkylate gasoline blending component.

SUMMARY

This application provides a process for reacting an iso-alkane, comprising:
a) partially converting one or more olefins in an olefinic feedstock to make a converted olefinic feedstock, wherein the converting is different from isomerization;
b) isolating from the converted olefinic feedstock:
  i. an enriched feed that has one or more linear internal olefins, and
  ii. one or more products having a boiling point of 150° C. or higher; and
c) alkylating the iso-alkane with the enriched feed to make an alkylate gasoline blending component.

BRIEF DESCRIPTION OF THE DRAWING

FIG. 1 is a process flow diagram of an embodiment of the invention.

DETAILED DESCRIPTION

The partially converting reduces undesired components in the olefinic feedstock. For example, the partially converting may convert one or more iso-olefins, one or more alpha-olefins, or a mixture thereof. In other embodiments the partially converting may reduce one or more of dienes, mercaptans, nitrogen & sulphur containing hydrocarbons, alpha-olefins and iso-olefins.

In one embodiment, the process for partially converting is different from olefin isomerization. Examples of processes that are useful for partially converting are dimerization, trimerization, oligomerization, metathesis, and catalytic distillation. In one example, the partially converting step oligomerizes one or more iso-olefins, while one or more linear internal olefins in the converted olefinic feedstock remain unconverted.

The olefinic feedstock can be any olefinic feedstock comprising undesired components that can be removed by the partially converting step. The undesired components, for example, can be iso-olefins, alpha-olefins, dienes, or mercaptans. In one embodiment, the olefinic feedstock comprises one or more iso-olefins, one or more alpha-olefins, or a mixture thereof. In one embodiment, the olefinic feedstock comprises C4 olefins.

Alkylating the iso-alkane is an exothermic reaction. To maintain the desired reaction temperature during alkylation, it is necessary to remove the reaction heat that is evolved. In some embodiments, the alkylation must be performed at relatively low temperatures, and sometimes even cooled in order to get the optimal product quality. A variety of methods are available for removing excess reaction heat. These methods are costly, and they include for example: 1) passing at least a portion of one product stream through a heat exchanger, and 2) cooling a reactor where the alkylating step occurs by evaporation. Other conventional cooling methods such as fans and cooling jackets are often needed. In some embodiments the temperature difference between the coolant and the reaction mixture during the alkylating is low, such that there can be a need for a large cooling surface, which can be prohibitively expensive.

In one embodiment the processes for reacting an iso-alkane produce a reaction heat that is evolved during the alkylating by a significantly lower amount compared to when the alkylating step is done with the iso-alkane and the olefinic feedstock without the partially converting step. The reaction heat that is evolved is at least 10% less, but in some embodiments can be at least 20%, at least 30%, at least 40%, at least 50%, and up to 90% less.

In one embodiment, the olefinic feedstock may be from a FCC unit or a coker unit. In other embodiments, the olefinic feed may be from a wax cracker, such as an autothermal cracking reactor. Olefins are typically produced in petroleum refineries using either the FCC process, the delayed coking process, or less often the fluidized coking process. In the future, as more waxy feeds become available from new sources (such as from Fischer-Tropsch processes such as Gas-to-Liquid, Coal-to-Liquid, or Biomass-to-Liquid), wax crackers will become more economic. FCC units use a fluidized catalyst system to facilitate catalyst and heat transfer between a reactor and a regenerator. Combustion of coke in the regenerator provides the heat necessary for the reactor. A good overview of examples of FCC units are described in "UOP Fluid Catalytic Cracking (FCC) and Related Processes", UOP 4523-7, June 2008; herein incorporated in its entirety.

A delayed or fluidized coker is an oil refinery processing unit that converts the residual oil from a vacuum distillation column or an atmospheric distillation column into low molecular weight hydrocarbon gases, naphtha, light and heavy gas oils, and petroleum coke. The process thermally cracks the long chain hydrocarbon molecules in the residual oil feed into shorter chain molecules. The coke from a coker can either be fuel grade (high in sulphur and metals) or anode grade (low in sulphur and metals).

The shorter chain molecules produced in a coker are richer in alpha olefin content than olefin feeds from a FCC unit. The high alpha olefin content in the shorter chain molecules produced in a coker unit form because cokers crack primarily by electron-promoted free radical mechanisms, whereas a FCC unit cracks by proton-promoted acid mechanisms. The shorter chain molecules from a coker also have a relatively high concentration of olefins. The higher the normal-paraffin content in the feed to the coker unit, the greater the alpha olefin content of the shorter chain molecules produced in the coker unit.

In one embodiment the coker unit is a delayed coker unit. A delayed coker unit is a type of coker unit whose process consists of heating a residual oil feed to its thermal cracking temperature in a furnace with multiple parallel passes. This cracks the heavy, long chain hydrocarbon molecules of the residual oil into coker gas oil and petroleum coke.

Delayed coker units may provide a higher content of alpha olefins than feeds from a FCC unit. The content of the alpha olefins is dependent on the normal-paraffin content in the feed to the delayed coker unit. Many oil refineries have delayed coker units and the shorter chain molecules produced in the delayed coker units are not in as high demand for conventional sulfuric or HF alkylation plants or for chemicals, so their availability and pricing are favorable.

The partially converting can be done with an ionic liquid catalyst. The ionic liquid catalyst is composed of at least two components which form a complex. The ionic liquid catalyst comprises a first component and a second component. The first component of the catalyst may comprise a Lewis Acid selected from components such as Lewis Acidic compounds of Group 13 metals, including aluminum halides, alkyl aluminum halide, gallium halide, and alkyl gallium halide (see International Union of Pure and Applied Chemistry (IUPAC), version 3, October 2005, for Group 13 metals of the periodic table). Other Lewis Acidic compounds besides those of Group 13 metals may also be used. In one embodiment the first component is aluminum halide or alkyl aluminum halide. For example, aluminum trichloride may be the first component of the ionic liquid catalyst.

The second component making up the acidic ionic liquid catalyst is an organic salt or mixture of salts. These salts may be characterized by the general formula Q+A−, wherein Q+ is an ammonium, phosphonium, boronium, iodonium, or sulfonium cation and A− is a negatively charged ion such as Cl−, Br−, ClO$_4^-$, NO$_3^-$, BF$_4^-$, BCl$_4^-$, PF$_6^-$, SbF$_6^-$, AlCl$_4^-$, TaF$_6^-$, CuCl$_2^-$, FeCl$_3^-$, HSO$_3^-$, RSO$_3^-$, SO$_3$CF$_3^-$, and 3-sulfurtrioxyphenyl. In one embodiment the second component is selected from those having quaternary ammonium halides containing one or more alkyl moieties having from about 1 to about 12 carbon atoms, such as, for example, trimethylamine hydrochloride, methyltributylammonium halide, or substituted heterocyclic ammonium halide compounds , such as hydrocarbyl substituted pyridinium halide compounds for example 1-butylpyridinium halide, benzylpyridinium halide, or hydrocarbyl substituted imidazolium halides, such as for example, 1-ethyl-3-methyl-imidazolium chloride.

In one embodiment the acidic ionic liquid catalyst is selected from the group consisting of hydrocarbyl substituted pyridinium chloroaluminate, hydrocarbyl substituted imidazolium chloroaluminate, and mixtures thereof. For example, the acidic ionic liquid catalyst can be an acidic haloaluminate ionic liquid, such as an alkyl substituted pyridinium chloroaluminate or an alkyl substituted imidazolium chloroaluminate of the general formulas A and B, respectively.

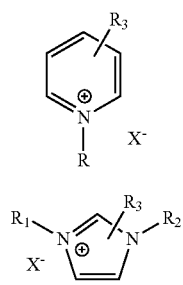

In the formulas A and B; R, R$_1$, R$_2$, and R$_3$ are H, methyl, ethyl, propyl, butyl, pentyl or hexyl group, X is a chloroaluminate. In the formulas A and B, R, R$_1$, R$_2$, and R$_3$ may or may not be the same.

In another embodiment the acidic ionic liquid catalyst can have the general formula RR'R" N H$^+$ Al$_2$Cl$_7^-$, wherein N is a nitrogen containing group, and wherein RR' and R" are alkyl groups containing 1 to 12 carbons, and where RR' and R" may or may not be the same.

The presence of the first component should give the ionic liquid a Lewis or Franklin acidic character. Generally, the greater the mole ratio of the first component to the second component, the greater is the acidity of the ionic liquid catalyst.

The ionic liquid catalyst may be either supported or unsupported. The term "supported" means that the catalyst is dispersed on a second material that enhances the effectiveness or minimizes the cost of the catalyst. Sometimes the support is merely a surface upon which the catalyst is spread to increase the surface area. More often, the support and the catalyst interact, affecting the catalytic reaction. Examples of supports that may be used include carbonaceous solids, silicaceous solids, polymers, inorganic oxides, and strongly acidic ion exchange resins.

In one embodiment, the ionic liquid catalyst is mixed with a hydrogen halide or an alkyl halide. The hydrogen halide or alkyl halide can boost the overall acidity and change the selectivity of the ionic liquid catalyst. It is believed that the alkyl halide decomposes under hydroconversion conditions to liberate Bronsted acids or hydrogen halides, such as hydrochloric acid (HCl) or hydrobromic acid (HBr). These Bronsted acids or hydrogen halides promote the alkylation reaction. Examples of alkyl halides are alkyl chloride, alkyl bromide, alkyl iodide, alkyl fluoride, and mixtures thereof. In one embodiment the alkyl halide is selected from the group consisting of alkyl chloride, alkyl bromide, alkyl iodide, and mixtures thereof. In one embodiment the halide in the hydrogen halide or alkyl halide is the same as a halide component of the acidic ionic liquid catalyst. In one embodiment the alkyl halide is an alkyl chloride. A hydrogen chloride or an alkyl chloride may be used advantageously, for example, when the acidic ionic liquid catalyst is a chloroaluminate.

In one embodiment, the process additionally includes isolating one or more products having a boiling point of 150° C. or higher, or 200° C. or higher, from the converted olefinic feedstock prior to the alkylating step. The isolating can comprise distillation to separate the products having different boiling point ranges. These one or more products can comprise a broad range of useful hydrocarbons, including naphtha, middle distillates, heavy naphtha, jet fuel, diesel fuel, light oil, and heavy oil. In one embodiment, the one or more products comprise a jet fuel, a diesel fuel, and a heavy oil. In one embodiment, these products isolated from the converted olefinic feedstock will contain olefins, as they will not have been substantially alkylated.

In another embodiment, the process additionally includes isolating an enriched feed that has one or more linear internal olefins from the converted olefinic feedstock. The alkylating step alkylates the enriched feed with an iso-alkane to make an alkylate gasoline blending component. In some embodiments the alkylate from the alkylating step is a low volatility gasoline blending component having a Research-method octane number (RON) of 86 or higher, 90 or higher, or even 92 or higher. The RON is determined using ASTM D 2699-07a. Additionally, the RON may be calculated [RON (GC)] from gas chromatography boiling range distribution data.

In one embodiment, the iso-alkane being alkylated comprises iso-butane, iso-pentane, or a mixture thereof.

A "gasoline blending component" may be either a gasoline or a naphtha hydrocarbon product suitable for blending into a gasoline. "Gasoline" is a liquid hydrocarbon used as a fuel in internal combustion gasoline engines. Gasoline engines take in a mixture of air and gasoline and compress it, then use a spark plug to ignite the mixture when it is compressed by the piston head in each cylinder. A "low volatility gasoline blending component" is a naphtha hydrocarbon product having a boiling range between 100° F. to 380° F. (38° C. to 193° C.) and a Reid Vapor Pressure of 2.5 psi (17.2 kPa) or less. In one embodiment the Reid Vapor Pressure is less than an amount defined by the equation RVP=−0.035×(50 vol % boiling point, ° C.)+5.8, in psi.

A "naphtha" is a lighter hydrocarbon product having a boiling range between 100° F. to 400° F. (38° C. to 204° C.). A light naphtha has a lower boiling range than a heavy naphtha. In the context of this disclosure, light naphtha is exemplified by hydrocarbons having boiling points in the range of 40-130° C., heavy naphtha is exemplified by hydrocarbons having boiling points in the range of 130-200° C., jet fuel is exemplified by hydrocarbons having boiling points in the range of 200-290° C., diesel fuel is exemplified by hydrocarbons having boiling points in the range of 290-360° C., light oil is exemplified by hydrocarbons having boiling points in the range of 316° C. and higher, and heavy oil is exemplified by hydrocarbons having a boiling point in the range of 360-about 550° C. The boiling range distribution of the hydrocarbon products may be determined by gas chromatography, such as by using ASTM Test Method D 2887-08. This test method is applicable to hydrocarbon products having final boiling points of 538° C. (or lower) at atmospheric pressure, and is limited to samples having initial boiling points greater than 55° C.

A "middle distillate" is a hydrocarbon product having a boiling range between 250° F. to 680° F. (121° C. to 360° C.). The term "middle distillate" includes the diesel, heating oil, jet fuel, and kerosene boiling range fractions. It may also include a portion of naphtha or light oil. A "jet fuel" is a hydrocarbon product having a boiling range in the jet fuel boiling range. The term "jet fuel boiling range" refers to hydrocarbons having a boiling range between 280° F. and 572° F. (138° C. and 300° C.).

In one embodiment the partially converting step removes one or more of dienes, mercaptans, alpha-olefins, and iso-olefins, and retains one or more internal olefins. The partially converting step improves the feedstock for the alkylating step, such that several improvements are realized, including: reduced heat evolution during the alkylating, less iso-butane formation during the alkylating, higher quality alkylate products from the alkylating (including, for example, low volatility alkylate gasoline blending component), and a broader range of products being produced. In addition, since the products of the partially converting step are less sensitive to a lower iso-alkane/olefin (I/O) ratio than alkylation, the fractionation delivering the I/O to the partially converting step could be designed for significantly reduced iso-alkane recycle flow giving substantial savings in the fractionation section as well. For example the I/O molar ratio during the partially converting could be maintained at less than 5/1, less than 2/1, or less than 1/1. For comparison the I/O molar ratios that are used during alkylating are typically greater than 5/1, which requires higher iso-alkane recycle flows. In one embodiment, the iso-alkane recyle is isolated from the effluent of the alkylating step by fractionation before being recycled to one or both of the partially converting or the alkylating steps. The partially converting and the alkylating may be done in either one or two separate reactors.

In one embodiment the wt % of the conversion of the one or more olefins in the olefinic feedstock are controlled to a desired level. Factors that can be adjusted to control the wt % conversion during the partially converting step include: the level of alkyl halide or hydrogen halide present during the partially converting, the length of time for the partially converting, the contact efficiency between the olefinic feedstock and the ionic liquid catalyst, the droplet size of the reactants, the temperature during the partially converting, the reactor design, and the choice of the olefinic feedstock. In one embodiment, at least 30 wt % of the one or more olefins in the olefinic feedstock are converted during the partially converting step. In other embodiments the wt % conversion of the one or more olefins in the olefinic feedstock during the partially converting is from 30 wt % to 95 wt %, from 40 wt % to 95%, from 50 wt % to 95%, from 60 to 95%, or from 70 to 95%.

In one embodiment, the reaction heat that is evolved during the alkylating is at least 20% less than if the alkylating step is done with the iso-alkane and the olefinic feedstock with the partially converting step. In other embodiments the reaction heat is at least 30% less, at least 40% less, at least 50% less, or even at least 60% less. By reducing the reaction heat that is evolved during the alkylating, significant savings due to reduced cooling requirements are achieved.

The following is a description of an embodiment of the invention with reference to FIG. 1:

An olefinic feedstock (1) is partially converted in a reactor (10) to form an effluent (3) comprising one or more linear internal olefins. An iso-alkane (2) may be optionally added to either the olefinic feedstock (1) or to the effluent (3). The effluent (3) is fed to an alkylation reactor (20) wherein the one or more linear internal olefins are alkylated to produce alkylate products (5). Products contained in the effluent (3) may be optionally isolated and withdrawn (4) before the effluent (3) is fed to the alkylation reactor (20).

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

EXAMPLES

Example 1

Iso-pentane was reacted with mixed FCC pentenes in the presence of N-butyl-pyridinium heptachlorodialuminate and HCl in a 100 ml continuously stirred tank reactor (CSTR) running at 1600 RPM at a temperature of 10° C. and 100 psi pressure. The iso-pentane was a refinery grade mixture comprising 76 wt % iso-pentane, 15 wt % n-pentane, 7 wt % n-butane, 2 wt % iso-hexanes and 1 wt % hydrocarbons lighter than n-butane.

The mixed FCC pentenes were withdrawn at a refinery and had the composition as shown in Table 1:

TABLE 1

Composition of refinery FCC pentene mixture

| Component | Wt % |
| --- | --- |
| n-Butane | 2 |
| Butenes (mostly 2-butene) | 7 |
| i-Pentane | 44 |
| n-Pentane | 6 |
| 1-Pentene | 1 |
| 2-Pentene | 16 |
| i-Pentenes | 20 |
| C6+ | 4 |

The iso-pentane stream (325 g/hr) was mixed with the mixed pentene stream (113 g/hr) and fed to the alkylation reactor together with N-butyl-pyridinium ionic liquid (60 g/hr) and HCl (approx. 0.8 g/hr). The effluent from the reactor was depressurized, the ionic liquid separated out, and the products fractionated. The volumetric mass balance showed that one kg olefin reacted with 1.93 kg iso-pentane to yield 0.68 kg iso-butane, 1.03 kg light naphtha (bp: 40-130° C.), 0.85 kg heavy naphtha (bp: 130-175° C.), 0.33 kg jet fuel (bp: 175-260° C.) and 0.04 kg heavier products (>260° C.)

Example 2

The same equipment and feeds as described in Example 1 were used in this experiment. The mixed pentenes were introduced into the CSTR at a rate of 105 g/hr and the ionic liquid at a rate of 60 g/hr. The HCl flow was varied in the range of 0.10-0.41 g/hr and the iso-pentane was fed at either of 293 g/hr or 146 g/hr during the course of the experiment. Though the lower iso-pentane feed rate appeared to give higher olefin conversion it did not seem to have a significant effect on the C6+ product composition. The reaction was conducted at 10° C. and 100 psi. The product was withdrawn as described in Example 1. The volumetric mass balance showed that 1 kg converted olefin yielded 0.21 kg light naphtha (bp 40-130° C.), 0.27 kg heavy naphtha (bp: 130-175° C.), 0.27 kg jet fuel (bp: 175-260° C.) and 0.25 kg heavier material (bp>260° C.). No iso-pentane was consumed and no iso-butane was produced. The unconverted olefin was predominantly 2-pentene which typically constituted more than 80% of the C5 olefins in the product.

Example 3

A premixed feed, modeling the products from a partial conversion process similar to that described in Example 2, contained 10 wt % 2-pentene, 89 wt % iso-pentane and 1 wt % n-pentane. The premixed feed was fed to the 100 ml CSTR at a rate of 374 g/hr together with 0.54 g/hr HCl and 120 g/hr ionic liquid and reacted at 10° C. and 100 psi. The volumetric mass balance on the products showed that one kg 2-pentene reacted with 1.56 kg iso-pentane to yield 0.09 kg iso-butane, 0.30 kg light naphtha (bp: 40-130° C.), 1.98 kg heavy naphtha (bp: 130-175° C.), 0.20 kg jet fuel (bp: 175-260° C.) and essentially no heavier products.

Example 4

A heat balance estimation illustrating the advantage of processing the mixed olefins under partial conversion conditions followed by alkylation with the remaining olefins at regular alkylation conditions was performed. It was assumed in this estimation that the partial conversion was operated at temperatures that do not require refrigeration.

The enthalpy of the reaction for the alkylation of iso-pentane with pentenes was assumed to be 66 KJ/mole olefin converted for all types of pentenes (1-pentene, 2-pentenes or iso-pentenes). Under regular refrigerated alkylation conditions this translates to a heat of reaction of 943 KJ/kg olefin. For a refrigerated alkylation reaction, all of this heat of reaction would have to be removed through refrigeration.

If part of the olefins were converted under partial olefin conversion at non refrigerated conditions, this would unload the refrigeration requirements accordingly. Partially converting the olefins under non refrigerated conditions will have much less negative effect on the heavier products formed than if the alkylate naphtha were formed under alkylation conditions with the unconverted mixed olefin feedstock. Thus if half of the olefins were converted under non-refrigerated partial conversion conditions the reaction heat that had to be removed by refrigeration would be lowered to 472 KJ/mole.

In addition, since the products of partial olefin conversion are less sensitive to the iso-alkane/olefin (I/O) ratio than alkylation, the fractionation delivering the I/O to the partial olefin conversion step could be designed for only half the iso-pentane recycle flow giving substantial savings in the fractionation section as well.

Example 5

Pure iso-butane (301 g/hr) was mixed with a mixed refinery FCC C4 stream at 139 g/hr. The mixed refinery FCC C4 stream had the following composition: 21 wt % 2-butene, 12% 1-butene, 11% iso-butene, 0.5% propene, 39% iso-butane, 11% n-butane, 1.5% propane, and 4% C5+. The mixture was processed (partially converted) at 10° C. and 50 psi with 0.09 g/hr HCl and 54 g/hr ionic liquid to make a converted olefinic feedstock. The olefin conversion was in the range of 70-91%. Based on mass balance on the products, 1 kg olefin reacted to yield approximately 0.10 kg light naphtha (bp 40-130° C.), 0.06 kg heavy naphtha (bp: 130-200° C.), 0.23 kg jet fuel (bp: 200-290° C.), 0.25 kg diesel fuel (290-360° C.), and 0.36 kg heavy oil (360-~550° C.). The unconverted olefins from different samples taken during the run were analyzed by GC analysis. The C4 olefin distributions in the samples of the converted olefinic feedstock taken during the run were found to be 9-20 wt % 1-butene, 80-91wt % 2-butene and 0 wt % iso-butene. For comparison, the C4 olefin distribution in the olefinic feedstock was 27% 1-butene, 48% 2-butene and 25% iso-butene.

Using in-house evaluation tools the alkylate quality that these C4 olefin mixtures would have yielded under typical iso-butane alkylation conditions using N-butyl-pyridinium heptachlorodialuminate and HCl as catalyst was estimated. It was estimated that the untreated olefinic feedstock C4's (27% 1-butene, 48% 2-butene and 25% iso-butene), when processed, would have yielded an alkylate with RON/MON=87/88. For comparison, it was estimated that the unconverted butenes in the converted olefinic feedstock (9-20wt %

1-butene, 80-91wt % 2-butene and 0 wt % iso-butene) would have yielded an alkylate with RON/MON=91-95/91-94.

We claim:

1. A process for reacting an iso-alkane, comprising:
   a) partially converting one or more olefins in an olefinic feedstock to make a converted olefinic feedstock, wherein the partially converting is done with an ionic liquid catalyst is selected from the group consisting of hydrocarbyl substituted pyridinium chloroaluminate, hydrocarbyl substituted imidazolium chloroaluminate, and mixtures thereof, wherein the converting is different from isomerization;
   b) isolating from the converted olefinic feedstock:
      i. an enriched feed that has one or more linear internal olefins, and
      ii. one or more products having a boiling point of 150° C. or higher; and
   c) alkylating the iso-alkane with the enriched feed to make an alkylate gasoline blending component.

2. The process of claim 1, wherein the isolating comprises distillation.

3. The process of claim 1, wherein the one or more products comprise a jet fuel.

4. The process of claim 1, wherein the one or more products comprise a diesel fuel.

5. The process of claim 1, wherein the one or more products comprise a heavy oil.

6. The process of claim 1, wherein the one or more products comprise a jet fuel, a diesel fuel, and a heavy oil.

7. The process of claim 1, wherein the alkylate gasoline blending component has a RON of at least 90.

8. The process of claim 1, wherein the iso-alkane comprises iso-butane.

9. The process of claim 1, wherein the olefinic feedstock comprises C4 olefins.

10. The process of claim 1, wherein the olefinic feedstock is from a FCC unit.

11. The process of claim 1, wherein the one or more products have a boiling point of 200° C. or higher.

12. The process of claim 1, wherein a fractionation delivering the iso-alkane and olefinic feedstock to the partially converting step could be designed for a significantly reduced iso-alkane recycle flow to the partially converting step.

13. The process of claim 1, wherein during the partially converting no iso-alkane is consumed and no iso-butane is produced.

14. The process of claim 1, wherein the ionic liquid catalyst is a butyl-pyridinium chloroaluminate.

* * * * *